(12) United States Patent
Rocker et al.

(10) Patent No.: US 8,586,102 B2
(45) Date of Patent: Nov. 19, 2013

(54) GERMICIDAL COMPOSITION

(75) Inventors: Ronald D. Rocker, Lincoln, NE (US);
Alvin Kershman, St. Louis, MO (US);
Jeff L. Shear, Bonita Springs, FL (US);
Paul A. Cusack, Buckinghamshire (GB)

(73) Assignee: Visions Marketing Group, Inc., Lincoln, NE (US)

( * ) Notice: Subject to any disclaimer, the term of this patent is extended or adjusted under 35 U.S.C. 154(b) by 290 days.

(21) Appl. No.: 12/661,339

(22) Filed: Mar. 16, 2010

(65) Prior Publication Data
US 2010/0233292 A1 Sep. 16, 2010

Related U.S. Application Data

(60) Provisional application No. 61/210,205, filed on Mar. 16, 2009.

(51) Int. Cl.
*A61K 33/30* (2006.01)
*A61P 31/02* (2006.01)
*A61P 17/02* (2006.01)

(52) U.S. Cl.
USPC .......................................................... 424/642

(58) Field of Classification Search
None
See application file for complete search history.

(56) References Cited

U.S. PATENT DOCUMENTS

| 4,469,674 | A | 9/1984 | Shah et al. |
| 5,760,052 | A | 6/1998 | Peacock |
| 5,780,064 | A | 7/1998 | Meisters et al. |
| 6,034,043 | A | 3/2000 | Fujiwara et al. |
| 6,248,370 | B1 | 6/2001 | Harris |
| 6,596,325 | B1 | 7/2003 | Vroom |
| 6,680,073 | B1 | 1/2004 | Tarbet |
| 2004/0042978 | A1 * | 3/2004 | Embro ............................. 424/52 |
| 2005/0100621 | A1 * | 5/2005 | Popp et al. .................... 424/776 |
| 2007/0197464 | A1 * | 8/2007 | Groenhof ........................ 514/53 |

FOREIGN PATENT DOCUMENTS

| EP | 2283805 A1 | 2/2011 |
| GB | 2141929 A | 1/1985 |
| JP | 2000-154111 * | 6/2000 |
| WO | 02/102352 A1 | 12/2002 |

OTHER PUBLICATIONS

Knovel: Stannous Fluoride. Retrieved online Sep. 10, 2011.*
Cole-Parmer Technical Library. Viscosity Values and Specific Gravity. Oct. 19, 2006.*
NTD Resource Center. Specific Gravity. Jan. 2007.*
PD Jelinek et al: "Eradication of bovine footrot by repeated daily footbathing in a solution of zinc sulphate with surfactant", Jun. 1, 2001, pp. 431-434, XP55003087, Retrieved from the internet: URS:http://onlinelinbrary.wiley.com/store/10.1111/j.1751-0813.2001.tb12991.x/asset/j.1751-0813.2001.tb12991.x.pdf?v=1&t=gqav1w8c&s=4f024ae70309a3de32794d0ca182e018905b8c23 [retrieved on Jul. 19, 2011].

* cited by examiner

*Primary Examiner* — Scott Long
*Assistant Examiner* — Sarah Alawadi
(74) *Attorney, Agent, or Firm* — Great/Venture Law, LLC; Linda L. Lewis; Dennis Donahue

(57) ABSTRACT

A germicidal lotion composition for treating or preventing diseases and wounds in humans or animals made by combining an aqueous phase comprising an aqueous solution or suspension containing a medicament, wherein the medicament is present in the solution or suspension in the range of about 0.015 to 80.0 wt. %; and an oil phase comprising an oil solution or suspension and a surfactant, wherein the surfactant is present in the oil in the range of from about 30 to 90 wt. %; wherein the aqueous phase is added to the oil phase in a weight ratio of about 3:1 to 99:1, and wherein the aqueous phase is added to the oil phase using low to medium shear mixing to provide the lotion.

17 Claims, No Drawings

GERMICIDAL COMPOSITION

This application claims the benefit of provisional patent application Ser. No. 61/210,205 filed Mar. 16, 2009.

FIELD OF THE INVENTION

The present invention relates to the treatment and prevention of infectious diseases and wounds in humans and animals using a germicidal composition.

BACKGROUND OF THE INVENTION

Infectious diseases of the hoof, such as hairy hoof warts (papillomatous digital dermatitis, or PDD), hoof rot (interdigital phlegmon), and stable hoof rot (interdigital dermatitis), are common in farm animals such as sheep, goats, horses, dairy cows, and beef cattle. Hoof warts were first reported in Italy in 1974, and since that time, have spread throughout the world. Since the late 1980's, hoof warts have been a significant source of bovine lameness, and have had a large negative economic impact on the dairy industry. For example, a recent study by the U.S. Department of Agriculture concluded that 47% of all dairy herds in the United States are affected by PDD, with 78% of those herds reporting their first cases in 1993 or later.

Clinically, PDD appears as a lameness outbreak within an animal herd. It is a superficial skin disease of the animal digit with variable presentation, depending on the stage of the lesion, from painful, moist, strawberry-like lesions to raised, hairy, wart-like lesions. It can result in severe lameness, and even death, if not properly treated. For dairy cows, hoof warts are also associated with losses in milk production, reproductive efficiency, and body weight.

Although PDD was originally believed to be caused by a virus, it is now believed that PDD is caused by one or more bacteria. Researchers have isolated two different spirochete species of bacteria from numerous PDD lesions, but have been unable to replicate the infectious disease in healthy animals using purified cultures of these organisms, signifying that additional causative agents and/or environmental conditions are necessary to bring about the disease.

Hoof rot, or interdigital phlegmon, is an infection of the soft tissue between the claws of the feet. In equine animals, it is also known as hoof thrush. Here, the term "hoof rot" will be used to indicate both hoof rot and hoof thrush. Hoof rot is caused by the anaerobic bacterium, *Fusobacterium necrophorum*. The anaerobes *Dichelobacter* (Bacteriodes) *nodosus* and *Prevotella melaninogenicus* have also been implicated. The bacteria invade the skin of the foot at injured or damaged skin areas, and initially cause a painful swelling of the skin between the claws. A fissure or crack then develops along the swollen area for part or all of the length of the interdigital space. If left untreated, hoof rot can enter the joints, bones, and/or tendons of the foot, making recovery from the infection unlikely. Animals with hoof rot can have a mild fever, loss of appetite and accompanying weight loss, and develop mild to severe lameness.

Interdigital dermatitis, or stable hoof rot, is generally a chronic inflammation of the skin in the area between the toes of the feet (interdigital cleft). This infection is caused by the bacterium *Dichelobacter nodosus*. The skin in the area of the interdigital cleft will appear puffy with a dry exudation which will cause a crust to form. The condition may occasionally cause lameness or heel crack/heel erosion but generally results in an alteration in the animal's gait.

At present, hoof warts, hoof rot and stable hoof rot are treated in several ways. The most effective treatment is the use of antibiotics, such as tetracycline, lincomycin, spectinomycin, penicillin, oxytetracycline, and ampicillin. These are topically applied to the affected area via use of footbaths, sprays, or footwraps for hoof warts and systemically for hoof rot. While antibiotics are effective in treating these infectious diseases, there are several drawbacks associated with antibiotic use. Antibiotics are expensive, and there is concern, especially with dairy cows, that the use of antibiotics may result in the presence of antibiotic residues in the animal or its milk. Further, extended use of antibiotics may result in the development of an antibiotic-resistant bacteria strain. It would be advantageous to use fewer dosages or lower dosages of antibiotics to effectively treat hoof rot.

The use of chemical-based germicides has also been tried as a treatment to prevent and/or control hoof rot, hoof warts, and stable hoof rot. Although some germicides, such as those containing copper sulfate and zinc sulfate, have some efficacy against hoof rot and stable hoof rot, they are ineffective against hoof warts. Quaternary ammonium compounds have also been used, but have never been proven to be effective against PDD. Such compounds are in addition ineffective at high dilutions, such as those used in foot baths, and many are expensive. Likewise, combinations of hydrogen peroxide and peracetic acid have been used, but also are not effective against PDD, and suffer from stability and storage problems. This chemical combination is also irritating to the hoof at the recommended treatment concentrations.

There have been anecdotal reports of success with formaldehyde against PDD, but controlled trials indicate that formaldehyde is less effective than antibiotics. Additionally, formaldehyde is classified as a carcinogen and toxin, and it is illegal to use it in some parts of the United States. Further, use of too high a concentration of formaldehyde can result in destruction of healthy hoof tissue, or can even lead to sloughing of the hoof. Thus, the use of formaldehyde is neither feasible nor effective in treating foot rot, stable foot rot, and PDD.

As stated above, footbaths comprising a germicide, such as copper sulfate or hydrogen peroxide, or even an antibiotic, are commonly used to prevent hoof rot, stable hoof rot, and/or PDD. Foot baths are typically dilutions of spray or footwrap compositions. However, foot baths are often ineffective, because the medicament washes off easily, or is tracked off as the animal walks away from the bath. Further, there is typically little wound protection provided by the treatment using a foot bath.

U.S. Pat. No. 5,780,064 discloses the use of an aqueous germicidal composition comprising a copper salt, a quaternary ammonium compound, and a peroxide, to treat and prevent PDD. This patent fails to disclose the presently claimed invention.

There is a need for a composition that is effective in preventing and treating foot rot, stable foot rot, and PDD, that is affordable. This composition must also minimize the use of antibiotics. There is a further need for a composition that can be used in a footbath effectively. Further, there is a need for germicidal compositions that are effective in prevent dental caries and gum disease.

SUMMARY OF THE INVENTION

The present invention relates to a germicidal composition for treating or preventing diseases and wounds in humans or animals comprising a lotion made by combining an aqueous phase comprising an aqueous solution or suspension containing at least one medicament, wherein the at least one medicament is present in the solution or suspension in the range of about 0.015 to 80.0 wt. %; and an oil phase comprising at least one oil solution or suspension and at least one surfactant, wherein the surfactant is present in the oil in the range of from about 30 to 90 wt. %; wherein the aqueous phase is added to the oil phase in a weight ratio of about 3:1 to 99:1, and wherein the aqueous phase is added to the oil phase using low to medium shear mixing to provide the lotion. This composition has a specific gravity based on water of greater than or equal to 1.0, and is particularly useful in treatment of animals using a foot bath.

DETAILED DESCRIPTION OF THE PREFERRED EMBODIMENTS

The germicidal composition of the present invention includes, but is not limited to medicaments such as formaldehyde, copper sulfate, antibiotics, zinc sulfate, stannous fluoride, or combinations, particularly, zinc salt and tin salt combinations. The composition can include topical anesthetics, such as benzocaine, lidocaine, tetracine, chloroprocaine and propoxicaine. Additionally, anti-inflammatories can be added, such as corticosteroid, glucocorticoid, hydrocortisone, betamethasone, desoximetasone, flucinoinide, aspirin, ibuprofen, acetaminophen, linoleic acid and ammonium bituminosulfanate. Herbal extracts that act as anti-inflammatories, such as green lip mussel extract and cranberry seed extract are also effective.

For a foot bath, the amount of medicament used can vary widely, depending on the specific treatment, and can be in the range of about 0.015 to 80.0% of the aqueous phase.

The oil phase is prepared from a hydrophobic solution or mixture containing at least one oil or petroleum distillate and at least one surfactant. The surfactant is preferably a non-water soluble surfactant having an HLB number of less than 4, and includes emulsifiers. Examples of suitable surfactants include oleic acid, acetylated monoglycerides, glycerol dioleate, sorbitan tristearate, glycerol monoleate, acetylated monoglycerides and various combinations of these. A preferred surfactant is Atmos® 300K, a food grade emulsifier. The surfactant is present in the oil phase in the amount of about 10 to 70%. The oil suitable for the oil phase is typically liquid or semi-solid at room temperature, and is compatible with wounds, the epidermis and the oral cavity. Such oils include plant oils, such as corn oil, canola oil, coconut oil, castor oil or olive oil, and animal fats such as tallow and lard. The oils include petroleum distillates, such as petrolatum and mineral oil. Mixtures of oils are also contemplated in the present invention.

Other additives suitable for the present invention include, but are not limited to, humectants, such as glycerine, colorings, flavorings, sweetners and abrasives.

The claimed germicidal composition is typically prepared using a planetary or counter rotating type mixer having a plastic or rubber lined mixing chamber or bowl equipped with a rubber or plastic coated wire whip or equivalent stirring device. The aqueous phase is blended and folded at relatively low shear (30-500 rpm's) into the phase, continuously forming a total coating or encapsulation of the antimicrobial water solution droplets by the oil. This process is enhanced significantly by the oil wet-able properties of the plastic or rubber lining of the mixing bowl or chamber. Rubber or plastic coating of the wire whip or equivalent stirring device improves the rate of processing.

The process of preparing the germicidal composition is typically conducted in 2 steps:

Step 1 produces a seed batch for further processing. The initial seed batch is produced by adding a small volume of oil phase to the lined mixing chamber or bowl at a sufficient depth that the wire whip or mixing device touches the oil while rotating. The wire whip is then engaged at rate of about 30 to 100 rpm's. The aqueous phase is added at a rate approximately equivalent to the initial volume of the oil solution per minute: That is, if the initial volume of the oil phase is 20 mL, then the aqueous phase is added at a rate of about 20 mL per minute while being mixed in at 30 to 100 rpm's. Once, the desired weight ratio of aqueous phase to oil phase is reached (about 3:1 to 99:1), this initial process step is concluded.

Step 2 begins with the seed batch of Step 1, at the desired final weight ratio of aqueous phase to oil phase. The volume of seed material needed for Step 2 is to about 5-20 volume % of the final mixing chamber volume. The mixing whip or equivalent stirring and folding device are engaged at a speed of about 50 to 500 rpm's. The oil and water phases are added separately and simultaneously to the starter batch at a ratio equal to that contained in the seed batch. The rate of adding the two separate solutions is about 1 to 5% of the mixing chamber capacity per minute. As the mixing bowl or chamber fills, excess liquid may be removed continuously without halting the process. Alternatively, the process can be halted for partial or entire contents removal. Once the process is halted and a portion of the contents removed, the retained material can be held for an extended period of time. At any time after halting, the process can be restarted to continuously produce the original product. Because coating of and encapsulation of the aqueous phase is almost immediate, and materials are mixed at final required ratio in step 2, all product produced at any time during step 2 is ready to use.

The high ratio of the aqueous phase to the oil phase may result in semi-liquid rheological properties ranging from thixotropic to pseudoplastic. These semi-liquid properties allow the material, though primarily composed of a free flowing water solution, to exhibit rapid flow only under pressure, and act as a solid once pressure is removed. This allows the medicament to stay in place on a wound or infection regardless of where it is located. Therefore, this germicidal composition may remain in place on the bottom of a cow's hoof or a wound on the side of a horse's leg without requiring a bandage or wrap.

Unlike liquid foams, which contain compressible gas and will eventually collapse, the presently claimed semi-liquid lotion composition may be hydraulic and non-compressible. Therefore, it may also be used to clean a wound or a topical infection site. It has the ability to lift and carry solids up to about 40% by volume without physical breakdown. This enables the composition to clean a wound and remove debris. Although, the debris is physically removed by rubbing in, then wiping out the composition, a significant amount of the medicament will be left on the wound. The composition may also function as a protective coating, hindering further infection.

A primary advantage of using the semi-liquid lotion composition for the treatment and prevention of PDD is to significantly reduce environmental contamination by antimicrobial actives resulting from current treatment methods. Environmentally unfriendly antimicrobials such as copper sulfate are commonly used in footbaths to prevent PDD.

Current bath treatments are usually based on adding antibacterial agents to 50 gallons water within a walk-through tub or tray apparatus. After approximately 250 cows walk through the bath, the total contents are dumped into the environment and replaced for the next 250 cows. Therefore, for a single bath treatment where copper sulfate is utilized at a rate of 5%, an average of 20 pounds of copper sulfate is dumped into the environment per 250 cows treated. Since copper sulfate footbath treatments are given on an average of three times a week, the quantity of copper sulfate dumped into the environment per year would be approximately 3,120 pounds per 250 cows. However, using the semi-liquid lotion composition containing 5% copper sulfate, the quantity of copper sulfate utilized per bath treatment would be approximately 3.0 pounds per 250 cows or 468 pounds/year, or a reduction of 85%. Further, because of the extended activity of the adherent lotion composition, bath treatments utilizing the semi-liquid lotion composition could be reduced to once or twice a week. This would be a reduction in copper sulfate use of 94 to 97%, or a savings of approximately 3,016 to 3,068 pounds of copper sulfate per 250 cows treated per year.

The presently claimed semi-liquid lotion composition typically has a specific gravity based on water greater than 1.0, and in a foot bath, will provide a layer of germicidal agent under a layer of water, on the bottom of the bath. This means that as a cow steps into the bath, its hoof travels through the water, washing off fecal contamination. Further, the lotion composition has water repellency properties that prevent the dispersion of the medicament throughout the water, which would dilute the medicament.

Reducing environmental contamination from problematic antimicrobials such as copper sulfate and formaldehyde is an important benefit of this invention, but equally important is the ability to optimize less effective and or as effective but more costly environmentally friendly medicaments, for the treatment of PDD as well as other topical infections and wounds. One specific combination of medicaments not previously used in a footbath application to treat PDD is both environmentally friendly and effective at treating PDD. This combination consists of a tin salt and a zinc salt. A preferred combination is that of stannous fluoride and zinc sulfate (monohydrate) in a molar ratio in the range of from 2:1 to 1:2 stannous fluoride to zinc sulfate.

A preferred molar ratio of stannous fluoride to zinc sulfate is from about 1:1 to 1:1.5. The combination of salts is present in the lotion in the range of about 0.01 to 99 wt %. A preferred range is from about 1 to 50 wt %, and a more preferred range is from about 1 to 35 wt %.

The combination of stannous fluoride and zinc sulfate in a molar ratio of 1:1.15 and at a concentration of 1.64 wt % $SnF_2$ and 1.89 wt % $ZnSO_4$ is equivalent or greater in the ability to inhibit the micro-organisms responsible for PDD than a standard solution of 5 wt % $CuSO_4$. Increasing the medicaments to 9.0 wt % $SnF_2$ and 10 wt % $ZnSO_4$, the ability to cure most PDD infections was found approximately equivalent to oxytetracycline. When the level of active was further increased to 15 wt % $SnF_2$ and 17.2 wt % $ZnSO_4$ within the mixture, the ability to cure the most severe PDD infections was essentially equivalent to oxytetracycline.

The stannous fluoride and zinc sulfate in the semi-liquid lotion may be a viable treatment for equine wounds. Minor to medium wounds may be both cleaned and treated successfully. The lotion containing a solution of 1.64 wt % stannous fluoride and 1.89 wt % zinc sulfate with up to 72 wt % glycerin added to the oil phase was used successfully to treat equine topical wounds without the need for wrapping a bandage on or around the treated site. Further, it was not necessary to have multiple applications a day, normally necessary when treating equine wounds because of the sustained antimicrobial activity of the lotion. In addition, the horses didn't lick off the lotion and flies and problematic insects did not attack the uncovered treated areas. This lotion containing any appropriate topical anti-microbial, may perform well, even uncovered.

The following examples of the invention are for illustration purposes only and are not to limit the claims or the scope of the invention in any manner.

EXAMPLES OF THE INVENTION

Example 1

Lotion for Bovine Foot Bath

TABLE 1

| Ingredients | % (w/w) |
|---|---|
| 1. De-ionized Water | 62.09 |
| 2. Avetech ™ 55 Mineral Oil | 12.38 |
| 3. Zinc Sulfate (monohydrate) | 9.10 |
| 4. Stannous Fluoride | 7.91 |
| 5. Atmos ® 300K (food grade emulsifier) | 7.43 |
| 6. Air Float Charcoal | 1.00 |
| 7. Keyfluor BO-1 (fluorescent pigment) | 1.00 |
| Total | 100.00% |

Method of Preparing the Lotion:
A. Preparing Aqueous Phase (79.09 wt % of Final Composition)

| De-ionized water | 2173.01 g |
|---|---|
| $ZnSO_4$ | 318.32 g |
| $SnF_2$ | 276.82 g |
| Total | 2768.15 g |

1. Add $ZnSO_4$ to warm water (approx. 26.7° C.) and stir 10 min. till dissolved.
2. Slowly add $SnF_2$ to $ZnSO_4$ solution and stir at least 20 min., then maintain minimal agitation throughout remainder of process.

B. Preparing Oil Phase (20.91 wt % of Final Composition)

| Light mineral oil | 433.30 g |
|---|---|
| Atmos ® 300K (surfactant) | 259.91 g |
| Charcoal powder | 35.14 g |
| Keyfluor OB-1 | 3.50 g |
| Total | 731.85 g |

1. Warm both liquids (mineral oil and surfactant) to 26.7° C.
2. Add Atmos® 300K to mineral oil and mix for 20 minutes at 26.7° C. Remove heat source.
3. Slowly add charcoal powder and Keyfluor OB-1 till fully dispersed. Maintain minimum agitation to keep powder in suspension throughout remaining process.
C. Forming the Seed Batch
1. Using a 5 qt lab Hobart type planetary lab/kitchen mixer with a rubber or plastic lined wire whip and rubber or plastic lined bowl add 200 g of oil phase and stir on #2 setting.

2. Add approx. 50 gm aqueous phase (directed towards the center of the bowl) and mix for 60 seconds or until fully dispersed, repeat 5 times then increase mixer speed to 4.

3. Continue as in step 1 at least 10 more cycles or until mix begins to "slosh around" (loses adherence to bowl wall). At this point add approximately 10 grams of oil phase (directed towards the side of the bowl). Once adherence to bowl returns, increase mix speed to 5, then add approximately 40 g aqueous phase till dispersed, followed by the addition of 10 g of oil phase.

4. Continue cycling between aqueous phase and oil phase at the rate of approx. 40 g of aqueous phase to approx 10 g oil phase, until all materials have been added. The last cycle should be the oil phase. The speed of mixing, and adjustments to addition rates are based on the "sloshing" affect, which indicates too much aqueous phase or that the aqueous phase is being added too quickly. "Sloshing" is easily corrected by addition of the oil phase directed to the sides of the bowl.

5. Once all of the phases have been added, the mixing speed is reduced to 4 and mixing is continued at least 15 minutes more. The seed started is removed from mixing bowl and stored for future batches. This product is designed to pour easily, so there is excess oil which after a few days appears on the surface as a film. This is not a stability issue. However, prior to use as a seed batch, thoroughly re-stir the entire contents of this batch with a hand whip before removing any portion for further use.

D. Preparation of the Lotion Using the Starter Seed.

1. Add at least 500 g of starter seed/3500 g batch to the mixing bowl.

2. Proceed as described in step 4 of C (above) until all of aqueous phase droplets are coated and encapsulated by the oil phase. Continue minimal mixing to ensure uniformity of the lotion.

The lotion of Example 1, Table 1, above, is viscous, pourable, and non-water dispersible, with a specific gravity of 1.12. It contains 9.10 wt % $ZnSO_4.H_2O$ and 7.91 wt % $SnF_2$.

This lotion is utilized in a footbath by pouring several gallons of the lotion into approximately 50 gallons of moving water within a footbath container. Because the lotion is both hydrophobic and denser than water, it rapidly sinks to the bottom of the bath container and spreads over the bottom of the bath. The salts in the lotion do not disperse into the water. The purpose of the moving water is to keep feces away from the lotion at the bottom of the bath container as the cattle walk through the bath. The charcoal is added to the lotion, because the cattle are spooked by the white lotion. The dark lotion may look more like mud to the cattle, which they are willing to walk through.

As the cattle walk through the bath, an average of about 25 grams of the lotion adheres to each hoof bottom. Even if a hoof comes in contact with the lotion multiple times, the level of adherence remains the same, because excess lotion sloughs off. Each cow leaves the bath with an average of about 100 grams of lotion on the bottom of her hoofs, or about 9.11 grams of $ZnSO_4$ (monohydrate) and about 7.92 grams of $SnF_2$ per cow, per bath.

The lotion will continue to adhere to the hoof bottom for several days, but most will be removed within 24 hours as a result of abrasion from contact with the ground. However, because the active is available via diffusion to the hoof bottom for an extended period of time, only one bath per week is required as maintenance against PDD. Current hoof treatments using copper sulfate typically include three baths per week.

Example 2

Wound Healing Formula

TABLE 2

| Ingredients | % (w/w) |
| --- | --- |
| 1. De-ionized Water | 17.97 |
| 2. Citation ™ 70 (mineral oil) | 4.20 |
| 3. Zinc Sulfate (monohydrate) | 1.76 |
| 4. Stannous Fluoride | 1.53 |
| 5. Atmos ® 300K (food grade emulsifier) | 2.62 |
| 6. Glycerin (humectant) | 71.92 |
| Total | 100.00% |

The Lotion of Example 2, Table 2 is used in the following treatments:

Fresh Open Wounds:

Fresh open wounds of a few hours or a few days old in most cases are bandaged the first 24-48 hours, with subsequent application once daily or once every other day without bandaging. These wounds respond with minimal swelling and normal healing patterns. Application of the lotion to fresh wounds does not cause any additional pain or irritation to already damaged tissue or surrounding normal tissue. The granulation bed established in fresh wounds is healthy, easily, managed and provides excellent opportunity to promote normal epithelialization. The scaring is minimal.

Chronic Older Wounds, Below the Carpus and Hock:

Chronic supurative, unhealthy granulating wounds especially on the metacarpal, metatarsal, pastern, and foot areas respond dramatically when the lotion is applied once daily. In most cases noticeable improvement in the granulating surface and supuration is observed within 24 hours. When initially applied under bandage, the positive response is even more pronounced. As long as there are no complications from foreign bodies or bone sequestration healing is uneventful. The protocol generally is daily application of lotion until epithelialization is complete. In some cases, the application is once every other day. Scarring in most cases is minimal, and tissue irritation is minimal. The pain reduction is dramatic.

Chronic Proud Flesh:

In most cases, Chronic Proud Flesh of several months duration responds to topical treatment alone to establish healthy granulation. In one case, where the animal had a history of four previous wound debridements in more uncontrollable granulation, when the lotion was applied under bandage for two weeks, and the bandage changed every 2nd or 3rd day, healthy granulation was established without further debridement.

Dermatitis:

Equine dermatitis, including but not limited to "scratches", girth itch, and localized dermatitis of unknown origin have responded remarkably with the lotion, even some that have been treated unsuccessfully for months with a myriad of different medications.

Canine ear-tip flybite dermatitis responds positively to the lotion.

Example 3

Dental Cleaning and Gum Treatment

| Ingredients: | % (w/w) in Formula |
|---|---|
| Oil Phase | |
| Citation 70 (mineral oil) | 6.04 |
| Atmos ® 300K (food grade emulsifier) | 3.28 |
| Green Lip Mussel Extract | 0.29 |
| Cranberry Seed Extract | 0.05 |
| Canine Grape | 0.24 |
| FONA Cherry Flavoring | 0.24 |
| FONA Cotton Candy Flavoring | 0.02 |
| FONA Milky Caramel Flavoring | 0.02 |
| Aqueous Phase | |
| Sorbitol Sweetner | 41.75 |
| $SnF_2$ | 1.58 |
| $SnSO_4$(monohydrate) | 1.83 |
| Water | 41.75 |
| Suspension 3 | |
| Titanium dioxide ($TiO_2$) | 0.97 |
| Pumice Grade FF (abrasive) | 1.93 |
| Total | 100.00 |

This dental cleaning composition is prepared as described above, wherein the above-described two step process of first preparing the seed batch, then, second, adding the oil phase and the aqueous phase in the desired ration to the seed batch. A third step is added at the end, where the Suspension 3 materials are added. This semi-liquid lotion is abrasive and is used to remove debris from teeth with brushing. It both cleans the teeth and provides long acting treatment of the gums and surrounding tissue by removing debris from the teeth, and then adhering to the surrounding tissue providing antibacterial effects with the $SnF_2$/$ZnSO_4$, and anti-inflammatory effect from the green lip mussel extract and the cranberry extract. The lotion, optionally, may just be applied to the gums without brushing, or in addition to brushing.

The invention claimed is:

1. A method of preparing a germicidal composition for treating or preventing diseases and wounds in humans or animals comprising a cream or lotion made by the process of combining:
   A) an aqueous phase comprising an aqueous solution or suspension containing stannous fluoride and zinc sulfate present in the solution or suspension in the range from about 0.015-80 wt. %; and
   B) an oil phase comprising at least one oil and at least one surfactant, wherein the at least one surfactant is present in the oil phase in the range of from about 30 to 90 wt. %;
   wherein the aqueous phase is added to the oil phase in a ratio of about 3:1 to 99:1, and the aqueous phase is added to oil phase in a mixing chamber using low to medium shear mixing to provide the cream or lotion.

2. A germicidal composition for treating wounds or treating and preventing hoof disease in animals comprising a lotion made by the process of:
   A) adding an aqueous phase comprising an aqueous solution or suspension containing stannous fluoride and zinc sulfate present in the solution or suspension in the range of about 0.015 to 80.0 wt. % to an oil phase in a ratio of 3:1 to 99:1;
   wherein the oil phase comprises at least one oil and at least one surfactant, wherein the at least one surfactant is present in the oil phase in the range of from about 30 to 90 wt. %; and
   B) mixing with low to medium shear to make the lotion;
   wherein the lotion comprises 1.64 to 15.0 weight % stannous fluoride and from 1.89 to 17.0 weight % zinc sulfate;
   wherein the molar ratio of stannous fluoride and zinc sulfate comprises a range of from 1:1 to 1:1.15;
   wherein the lotion comprises a specific gravity of equal to or greater than 1.0; and
   wherein the lotion is hydrophobic, pourable, viscous and adheres to a hoof or wound without a bandage or wrap.

3. The composition of claim 2, wherein the lotion contains charcoal to color the lotion.

4. The composition of claim 2, wherein the lotion further comprises up to 72% weight % glycerin.

5. A seed batch for a germicidal composition for treating wounds or treating and preventing hoof disease in animals comprising a lotion made by the process of:
   A) adding to a mixing chamber a small amount of an oil phase comprising at least one oil and at least one surfactant, the at least one surfactant is present in the oil phase in the range of from about 30 to 90 wt. %;
   B) adding to the oil an aqueous phase comprising an aqueous solution or suspension containing stannous fluoride and zinc sulfate present in the solution or suspension in the range of about 0.015 to 80.0 wt. % with low to medium shear mixing in a ratio of 3:1 to 99:1 to form a volume of seed batch about 5 to 20 volume % of the total volume of the mixing chamber;
   wherein the lotion comprises from 1.64 to 15.0 weight % stannous fluoride and from 1.89 to 17.0 weight % zinc sulfate;
   wherein the lotion comprises a molar ratio of stannous fluoride and zinc sulfate in the range of from 1:1 to 1:1.15; and
   wherein the lotion comprises a specific gravity of equal to or greater than 1.0.

6. The seed batch of claim 5 further comprising, adding to the seed batch in the mixing chamber the oil phase and the water phase separately and simultaneously mixing at a ratio of 3:1 to 99:1 to provide a germicidal composition.

7. The germicidal composition of claim 6 wherein the composition is hydrophobic, pourable, viscous and adheres to a hoof or wound without a bandage or wrap.

8. The germicidal composition of claim 6, wherein 5 to 20 volume % of the total volume of the mixing chamber is set aside to be the seed batch for the next batch of germicidal composition.

9. The germicidal composition of claim 6, wherein the surfactant comprises a non-water soluble surfactant having an HLB number of less than about 4.

10. The germicidal composition of claim 9, wherein the surfactant comprises emulsifiers.

11. The germicidal composition of claim 6, wherein the surfactant is selected from the group consisting of oleic acid, acetylated monoglycerides, glycerol dioleate, sorbitan tristearate, glycerol monooleate, acetylated monoglycides and combinations thereof.

12. The composition of claim 2, wherein the surfactant comprises a non-water soluble surfactant having an HLB number of less than about 4.

13. The germicidal composition of claim 12, wherein the surfactant comprises emulsifiers.

14. The germicidal composition of claim 2, wherein the surfactant is selected from the group consisting of oleic acid, acetylated monoglycerides, glycerol dioleate, sorbitan tristearate, glycerol monooleate, and combinations thereof.

15. The composition of claim 6 lotion further comprises up to 72 weight % glycerin.

16. The composition of claim 6, further comprising charcoal to color the lotion.

17. A germicidal composition for treating wounds or treating and preventing hoof disease in animals comprising a lotion made by the process of:
A) adding an aqueous phase comprising an aqueous solution or suspension containing stannous fluoride and zinc sulfate present in the solution or suspension in the range of about 0.015 to 80.0 wt. % to an oil phase in a ratio of 3:1 to 99:1;
wherein the oil phase comprises at least one oil and at least one surfactant, the at least one surfactant present in the oil phase in the range of from about 30 to 90 wt. %; and
B) mixing with low to medium shear to make the lotion;
wherein the surfactant comprises a non-water soluble surfactant having an HLB number of less than about 4;
wherein the lotion comprises from 1.64 to 15.0 weight % stannous fluoride and from 1.89 to 17.0 weight % zinc sulfate;
wherein the lotion comprises a molar ratio of stannous fluoride and zinc sulfate in the range of from 1:1 to 1:1.15;
wherein the lotion further comprises charcoal to color the lotion;
wherein the lotion comprises a specific gravity of equal to or greater than 1.0;
and wherein the lotion is hydrophobic, pourable, viscous and adheres to a hoof or wound without a bandage or wrap.

* * * * *